(12) United States Patent
Diaz Alperi et al.

(10) Patent No.: US 9,211,270 B2
(45) Date of Patent: Dec. 15, 2015

(54) METHOD FOR IMPROVING THE EFFICACY OF CURCUMINOIDS AND THEIR ANALOGS

(71) Applicant: ASAC Compañía de Biotecnología e Investigación, S.A., Alicante (ES)

(72) Inventors: Joaquin Diaz Alperi, Alicante (ES); Ana Adela Ramirez Bosca, Alicante (ES); August Bernd, Bingen (DE)

(73) Assignee: ASAC Compañia de Technologia e Invertigación, S.A., Alicante (ES)

( * ) Notice: Subject to any disclaimer, the term of this patent is extended or adjusted under 35 U.S.C. 154(b) by 0 days.

(21) Appl. No.: 14/284,475

(22) Filed: May 22, 2014

(65) Prior Publication Data

US 2014/0257170 A1    Sep. 11, 2014

Related U.S. Application Data

(63) Continuation of application No. 12/797,059, filed on Jun. 9, 2010, now Pat. No. 8,748,494, which is a continuation-in-part of application No. PCT/ES2008/000787, filed on Dec. 19, 2008, which is a continuation of application No. PCT/ES2007/000753, filed on Dec. 21, 2007.

(30) Foreign Application Priority Data

Feb. 22, 2008   (EP) .................................... 08003253
Oct. 31, 2008   (EP) .................................... 08019146

(51) Int. Cl.
| | | |
|---|---|---|
| *A01N 35/00* | (2006.01) | |
| *A61K 31/12* | (2006.01) | |
| *A61K 31/122* | (2006.01) | |
| *A61K 36/9066* | (2006.01) | |
| *A61N 5/06* | (2006.01) | |

(52) U.S. Cl.
CPC .......... *A61K 31/122* (2013.01); *A61K 36/9066* (2013.01); *A61N 5/06* (2013.01); *A61N 5/062* (2013.01)

(58) Field of Classification Search
None
See application file for complete search history.

(56) References Cited

U.S. PATENT DOCUMENTS

| | | | |
|---|---|---|---|
| 5,401,777 | A | 3/1995 | Ammon et al. |
| 5,891,924 | A | 4/1999 | Aggarwal |
| 5,897,865 | A | 4/1999 | Nguyen |
| 5,925,376 | A | 7/1999 | Heng |
| 6,440,468 | B1 | 8/2002 | Quintanilla Almagro et al. |
| 6,673,843 | B2 | 1/2004 | Arbiser |
| 6,841,177 | B1 | 1/2005 | Quintanilla Almagro et al. |
| 7,067,159 | B2 | 6/2006 | Newmark |
| 7,220,438 | B2 | 5/2007 | Quintanilla Almagro et al. |
| 7,556,818 | B1 | 7/2009 | Heng |
| 2001/0025034 | A1 | 9/2001 | Arbiser |
| 2001/0051184 | A1 | 12/2001 | Heng |
| 2008/0058426 | A1 | 3/2008 | Majeed et al. |

FOREIGN PATENT DOCUMENTS

| | | |
|---|---|---|
| EP | 1133992 | 9/2001 |
| EP | 1837030 A1 | 9/2007 |
| WO | 03/039452 A2 | 5/2003 |

OTHER PUBLICATIONS

Cecil's Textbook of Medicine, pp. 1060-1074, 2000.*
Kleinpenning MM et al. "Narrowband ultraviolet B therapy in psoriasis: randomized double-blind comparison of high-dose and low-dose irradiation regimens". Br J Dermatol. Dec. 2009; 161(6): 1351-6. Epub Apr. 10, 2009.
Cui BN. et al., "Clinical efficacy of narrow band ultraviolet bin combined with yuyin recipe in treating psoriasis vulgaris". Zhongguo Xi Yi Jie He Za Zhi (2008), 28(4):355-7 (abstract).
Valkova S. "UVB phototherapeutic modalities. Comparison of two treatments for chronic plaque psoriasis." Acta Dermatovenerol Alp Panonica Adriat (2007), 16(1):26-30 (abstract).
Sivanesan et al. "Randomized, double-blind, placebo-controlled evaluation of the efficacy of oral psoralen plus ultraviolet A for the treatment of plaque-type psoriasis using the Psoriasis Area Severity Index score (improvement of 75% or greater) at 12 weeks". J Am Acad Dermatol (Nov. 2009), 61:793-798.
Kurd et al. "Oral curcumin in the treatment of moderate to severe psoriasis vulgaris: A prospective clinical trial.". J Am Acad Dermatol. (Apr. 2008), 58(4):625-31. Epub Feb. 4, 2008.
Toennesen et al. "Studies on curcumin and Curcuminoids". Z Lebensm Unters Forsch (1986),183:116-122.
Casacci et al. "Comparison between 308 nm monochromatic excimer light and narrowband UVB phototherapy (311-313 nm) in the treatment of vitiligo a multicentre controlled study." JEADV (2007), vol. 21:956-963.
Dujic et al. "Low concentrations of Curcumin Induce Growth Arrest and Apoptosis in Skin Karatinocytes only in combination with UVA or visible light."Journal of Investigate Dermatology (2007) 127:1992-2000.
Garcea, et al. "Detection of curcumin and its metabolites in hepatic tissue and portal blood of patients following oral administration" Br J Cancer. (Mar. 8, 2004), 90(5):1011-15.
Anand et al. "Biological activities of curcumin and its analogues (Congeners) made by man and Mother Nature." Biochem Pharmacol. (Dec. 1, 2008), 76(11):1590-611. Epub Aug. 19, 2008. (Abstrac.

(Continued)

*Primary Examiner* — Anna Pagonakis
(74) *Attorney, Agent, or Firm* — Rick Matos; Innovar, L.L.C.

(57) ABSTRACT

The invention relates to a method for increasing the therapeutic efficacy of curcuminoids and analogs. More specifically, the invention relates to a method for increasing the therapeutic efficacy of systemically administered formulations that contain curcuminoids and the equivalent therapeutics thereof. The method is characterized in that together with the administration of the formulation the patient is irradiated with visible, and optionally ultraviolet, radiation during a treatment. The invention also relates to phototherapy devices that emit visible radiation over a surface area greater than 0.2 m$^2$ with an irradiance of more than 2 mW/cm$^2$, the devices being suitable for use in the treatment of proliferative diseases, particularly moderate-to-severe psoriasis or tumor processes.

36 Claims, No Drawings

(56) References Cited

OTHER PUBLICATIONS

Bissonnette et al. "Systemic photodynamic therapy with aminolevulinic acid induces apoptosis in lesional T lymphocytes of psoriatic plaques". J Invest Dermatol (2002), 119:77-83.

Shehzad et al."Efficacy of concomitant use of PUVA and Methotrexate in diseases clearance time in plaque type psoriases". J Pak Med. Assoc. (2004), 54(9):453-5. (Abstract).

Barzegari et al. "A comparison of three times vs five times weekly narrowband ultraviolet B therapy for the treatment of chronic plaque psoriasis". Photodermatol. Photoimmunol. Photomed. (Feb. 2010), 26(1):10-15. (Abstract).

Hasegawa et al. "Efficacy of 308-nm excimer light for Japanese patients with psoriasis". J. Dermatol. (Nov. 2009), 36(11):579-582. (Abstract).

Seckin et al. "Topical 8-methoxypsoralen increases the efficacy of narrowband ultraviolet B in psoriasis". PPhotodermatol. Photoimmunol. Photomed. (Oct. 2009), 25(5):237-241. (Abstract).

Kwon et al. "A retrospective review of 20% vs 10% incremental narrowband UVB regimens to treat psoriasis in skin phototypes III-V Koreans". Photodermatol. Photoimmunol. Photomed. (Jun. 2009), 25(3):124-7. (Abstract).

Koek et al. "Home versus outpatient ultraviolet B phototherapy for mild to severe psoriasis: pragmatic multicentre randomized controlled non-inferiority trial (PLUTO study)". BMJ (May 2009), 338:b1542. (Abstract).

Kircik et al. "Treatment of moderate to severe plaque psoriasis with concomitant efalizumab and narrow-band ultraviolet B phototherapy". J. Drugs Dermatol. (Oct. 2008), 7(10):947-952. (Abstract).

Toennesen et al. "Studies on curcumin and curcuminoids. IX: Investigation of the photobiological activity of curcumin using bacterial indicator systems". J. Pharm. Sci. (May 1987), 76(5):371-3. (Abstract).

Shishodia et al. "Curcumin: getting back to the roots". Ann N Y Acad Sci (Nov. 2005), 1056:206-17. (Abstract).

Dalton et al., entitled "Clinical Pharmcokinetics of 5-Aminolevulinic Acid in Healthy Volunteers and Patients at High Rish of Recurrent Bladder Cancer" in J. Pharm. Exp. Therap. (2002), 301(2), 507-512.

Wilken et al. ("Curcumin: A review of anti-cancer properties and therapeutic activity in head and neck squamous cell carcinoma"; Molecular Cancer (Feb. 2011), 10:12, 1-19; Abstract).

Jiang et al. ("Curcumin induces apoptosis in immortalized NIH 3T3 and malignant cancer cell lines"; Nutr. Cancer, (1996), 26(1), 111-120; Abstract).

Mehta et al. ("Antiproliferative effect of curcumin (diferuloylmethane) agains human breast tumor cell lines"; Anticancer Drugs (Jun. 1997), 8(5), 470-481; Abstract).

Huang et al. ("Inhibitory effects of dietary curcumin on forestomach, duodenal and colon carcinogenesis in mice"; Cancer Res., (Nov. 1994), 54(22), 5841-5847; Abstract).

Dorai et al. ("Therapeutic potential of curcumin in human prostate cancer: II. Curcumin inhibits tyrosine kinase activity of epidermal growth factor receptor and depletes the protein"; Mol. Urol., (2000), 4(1), 1-6; Abstract).

Li et al. ("Effects of curcumin on proliferation and apoptosis in human hepatic cells"; Zhonghua Gan Zang Bing Za Zhi, (Dec. 2002), 10(6), 449-51; Abstract).

Wu et al. ("Anticancer activities of curcumin on human Burkitt's lymphoma"; Zhonghua Zhong Liu Za Zhi, (Jul. 2002), 24(4), 348-352; Abstract).

O'Sullivan-Coyne et al. ("Curcumin induces apoptosis-independent death of oesophageal cancer cells"; Br. J. Cancer (Nov. 2009), 101(9), 1585-1595; Abstract).

\* cited by examiner

METHOD FOR IMPROVING THE EFFICACY OF CURCUMINOIDS AND THEIR ANALOGS

CROSS-REFERENCE TO EARLIER FILED APPLICATIONS

The present application is a continuation of and claims the benefit of U.S. application Ser. No. 12/797,059, filed Jun. 9, 2010, which is a continuation-in-part of and claims the benefit of PCT International Application No. PCT/ES08/000787 filed Dec. 19, 2008, which claims the benefit of PCT/ES07/000753 filed Dec. 21, 2007, and European Applications No. EP08003253 filed Feb. 22, 2008 and No. EP08019146 filed Oct. 31, 2008, the entire disclosures of which are hereby incorporated by reference.

TECHNICAL FIELD OF THE INVENTION

The present invention describes a method for improving the therapeutic efficacy of formulations comprising Curcuminoids and their analogs when they are administered systemically. The method is characterized in that quantifiable visible and/or ultraviolet radiation is periodically irradiated upon a patient undergoing curcuminoid therapy for the treatment of a disease or disorder.

The present invention also describes a phototherapy device for emitting visible light radiation over a surface greater than $0.20\ m^2$ with an irradiance higher than $2\ mW/cm^2$, and its use in the treatment of dermatological and/or proliferative diseases.

BACKGROUND OF THE INVENTION

Curcumin and its therapeutic analogs (*Curcuma* rhizomes, extracts, Curcuminoids (desmethoxycurcumin, bisdesmethoxycurcumin, tetrahydrocurcumin), prodrugs and metabolites) have been shown to exhibit various pharmacological activities such as antioxidant and antiproliferative properties, induction of apoptosis, etc. Based on in vitro results, Curcumin offers the potential to act as a drug for the treatment of pathologies described in the state of the art such as psoriasis, cancer, inflammatory processes, vitiligo, etc.

Curcumin and its equivalents reportedly exhibit very low oral bioavailability. *Br J Cancer.* 2004 Mar. 8; 90(5):1011-5 discloses that after oral administration, only trace levels of its metabolites were found in liver tissue, and no curcumin was found. Therefore, an artisan would presume that Curcuminoids lack in vivo efficacy following oral administration, and efficacy is much reduced in vivo as compared to in vitro results. *J Am Acad Dermatol.* 2008 April; 58(4):625-31 corroborates this finding (published after priority date). The document reports that a phase II, uncontrolled trial in patients older than 18 years who were orally administered 4.5 g Curcuminoids/day had to be abandoned because only 17% of patients responded to treatment with a reduction of 75% of psoriatic plaque.

Due to the demonstrated lack of efficacy following oral administration, an artisan of skill, such as cited in Amand et al *Biochem Pharmacol.* 2008 Aug. 19. [Epub ahead of print] (published after priority dated), would be motivated to search for solutions for improving in vivo efficacy of Curcumin oral formulations and to discover a "supercurcumin", if such a compound was available. Solutions to the lack of oral efficacy that have been found include, for example, structural modifications for improving Curcumin absorption (EP1837030), new galenic formulations (WO/2008/030308), and the administration of high doses in combination of other active ingredients (U.S. Pat. No. 5,925,376, WO03088986).

Phototherapy is a useful tool for treatment of various diseases such as proliferative and/or dermatological pathologies (psoriasis, cancer), acne and jaundice. Phototherapy activity is based on the structural changes in compounds induced by the radiation. Phototherapy is used for the treatment of jaundice in newborn. The newborn, having a body surface area of $0.20\ m^2$, is irradiated with visible light, preferably with an emission maximum at 550 nm, and an irradiance close to 40 $W/m^2$ in order to degrade bilirubin.

Actinic light (maximum emission at 420 nm) is used for acne treatment based on its bactericide properties. The surface area irradiated by these lamps is less than $400\ cm^2$.

Photochemotherapy, concomitant administration of psoralens and irradiation with ultraviolet light, is the treatment of choice for moderate to severe psoriasis, but the treatment has many secondary effects: hyperpigmentation, hepatotoxicity, hypersensitization reactions. Sivanesan et al. (*J. Am. Acad. Dermatol.* (2009), 61, 793-8) discloses the results of a clinical study on the efficacy of UVA radiation alone as compared to UVA radiation in combination with orally administered psoralen capsules in the treatment of psoriasis. Even after 12 weeks, the UVA radiation alone did not reduce in any patient the PASI score by 75% in the psoriasis area. Moreover, the irradiated dose must be carefully adjusted in order to minimize the carcinogenic property of UV radiation.

Aminolevulinic acid combined with blue light phototherapy has been shown to be effective in the treatment of actinic keratosis. *J Invest Dermatol.* 2002 July; 119(1):77-83 describes its systemic administration (oral) in combination with 1-20 $J/cm^2$ visible light (LED (light emitting diode)—maximum emission at 417 nm) for the treatment of psoriasis, but the efficacy is limited and said treatment cannot be used in moderate to severe psoriasis. The results obtained showed that on 15 plaques of 1.5*1.5 cm ($34\ cm^2$) the severity of the plaques was only improved by 42% compared to baseline.

In in vitro assays and trials employing topical administration, photoradicals or degradants generated in situ by irradiation are unstable and are those responsible for pharmacological activity. Photosensitization after the administration of a photosensitizing agent administered systemically cannot be produced immediately; the drug must first be metabolized and, later, must be photoactivated. In summary, effectiveness of phototherapy cannot be predicted a priori, because it depends on bioavailability of the drug administered and on pharmacological activity of artifacts formed during the irradiation.

In the particular case of Curcumin, the state of the art shows that it has very low bioavailability, and further, it is known that Curcuminoids are degraded by visible-ultraviolet light, both in solution and solid state. The major degradation product is a cyclization of Curcumin by loss of 2 hydrogen atoms.

Psoriasis is a chronic disease and its etiology is not fully understood. Clinically, psoriasis is characterized by the of presence patches or erythematosus plaques with a dark reddish color, delimited borders and often covered with scales that are due to the changes in cellular proliferation marked by genetic and immunological mechanisms. Thus, psoriasis may be considered as a proliferative disease.

The severity of psoriasis is determined by the PASI index (Psoriasis Area Severity Index), BSA (Body Surface Area) and PGA (Physican Global Assessment). PASI is an objective index and is used to evaluate drug therapeutic efficacy. According to PGA, psoriasis may be classified into:

Mild or moderate psoriasis: lesions are under control with topical treatment; BSA<10%, PASI<10, Moderate psoriasis: it is still possible to control the disease with topical treatment; BSA>10%, PASI 10 or higher, Moderate to Severe psoriasis: topical treatment cannot control the disease; BSA>10%, PASI 10-20; very thick lesions in areas that are difficult to treat, Severe psoriasis: systemic treatment necessary to control the disease; BSA>20%, or PASI>20; important local lesions of high thickness with BSA>10%.

EMEA Guidelines criteria establish that patients are considered responders when PASI reduction is at least 75% of the baseline.

Currently, there is no widely accepted animal model to assess the in vivo efficacy of pharmaceuticals in the treatment of psoriasis. Drug efficacy must be tested in people who suffer from psoriasis or in animal models by studying inhibition of tumor proliferation, for example, the cell proliferation of the A431 cell line (cells of epidermal carcinoma).

Efalizumab, recently authorized for psoriasis treatment, has some efficacy. In 12 week studies, 22-35% of patients reached a score of PASI-75 (improvement of 75%).

Photochemotherapy with Aminolevulinic acid and visible light only showed 42% improvement in psoriatic plaques compared to baseline. According to EMEA guidelines, the treatment lacks effectiveness, in particular in the treatment of moderate to severe and severe psoriasis.

Psoriasis patients tend to hide their lesions and often abandon topical treatments, because these stain clothes. In accordance with an opinion poll conducted by European Federation of Psoriasis Associations, there is a high degree of dissatisfaction in psoriasis sufferers regarding the efficacy of such treatments for this disease and they give up treatment.

EP1133992 describes the photosensitizing activity of visible-UV light on Curcuminoids, administered in the form of a topically applied extract, for the treatment of psoriasis. The cream described in EP1133992 must be applied before the radiation, but the treatment is abandoned by patients because the *Curcuma* extracts are colored and stain clothes. Moderate to severe psoriasis that involves more than 10% of body surface area cannot be treated by the topical route because the patients do not respond to treatments administered via the topical route. The '992 patent discloses irradiation of cultured human keratinocytes with UV radiation (UVA range 340-390 nm, UVB range 290-310 nm, 150 mJ/cm$^2$ or 1 J/cm$^2$), and the irradiation of psoriatic skin in human patients using visible light (weekly sessions of irradiation with a 440 nm lamp (radiation intensity unspecified) with 3 min irradiation periods).

The results obtained in phototherapy by the topical administration route cannot be extrapolated to systemic administration as described for aminolevulinic acid.

Another type of phototherapy currently being used is photodynamic therapy. The drug is administered and the patients irradiated with a pulsed light having a high irradiance of approximately 300 mW/cm$^2$. The light is administered on a small surface for short time interval, irradiating 100 J/cm$^2$, but the method causes pain to patients.

Exemplary phototherapy devices currently available include:

UV-Cabins emitting an irradiance of 2-30 mW/cm$^2$ of ultraviolet light over the whole body surface area of the patient, but without emitting visible light, devices emitting visible light irradiating a small surface area of approximately 500 cm$^2$, but always less than 10% body surface area of an adult, and Gas Discharge Lamps having an emission range of 400-550 nm and which may be fitted to UV-cabins, for example, Phillips TLK 40 W/03 or TLK 140 W/03 but these lamps are used for photo printing and for aquarium lighting.

There are also filters for selectively absorbing certain wavelengths and transmitting radiations of 400-430 nm.

Given that to date no drug has shown efficacy in phototherapy with visible light following oral administration of the drug, artisans in the field would not be motivated to combine the low intensity radiation equipment described above in order to manufacture a phototherapy device that emits visible light having an irradiance higher than 2 mW/cm$^2$ over a surface greater than 0.2 m$^2$ or greater than 40 cm$^2$, wherein the device can be used to treat psoriasis, cancer, tumor, vitiligo or other disorder or disease.

SUMMARY OF THE INVENTION

An object of the invention is to improve the therapeutic efficacy of Curcuminoids and their therapeutic equivalents when they are administrated systemically. This improvement can be achieved by combining systemic administration of Curcuminoids with phototherapy employing quantifiable device-generated visible light radiation.

Another object of the invention is to provide a method of reducing the PASI score in a psoriatic patient. The invention provides a treatment method whereby PASI reduction in the patient is higher than 75%, and it is achieved in at least 80% of patients in a population of patients in need thereof, with a probability higher than 80% after repeated device-generated light irradiation with radiation unit doses of 1-18 J/cm$^2$, of either device-generated ultraviolet light and/or device-generated visible light, thereby meeting the efficacy criteria of the EMEA. The combined use of systemic administration of curcuminoids and device-generated visible light radiation and/or device-generated ultraviolet light radiation provides additional benefits in the treatment of diseases and disorders.

An aspect of the invention provides a method of treating a disease or disorder having an etiology associated with excessive cell proliferation, the method comprising: a) systemically administering to a subject, having an affected area with a disease or disorder having an etiology associated with excessive cell proliferation, an effective amount of curcuminoid according to a dosing regimen; b) exposing 0.2 m$^2$ or greater or 40 cm$^2$ or greater of skin of the subject to device-generated visible light radiation having an irradiance of 2 mW/cm$^2$ or higher to achieve a unit radiation dose of 1-18 or 1-36 J/cm$^2$ per exposure; and c) repeating steps a) and b) until a cumulative radiation dose of 150 to 560 J/cm$^2$, or 150-600 J/cm$^2$ during a total treatment period is achieved.

Another aspect of the invention provides a method of treating psoriasis, the method comprising: a) orally administering to a subject having an affected area with psoriasis an effective amount of curcuminoid per day; b) exposing the affected area to device-generated visible light radiation having an irradiance of 2 mW/cm$^2$ or higher to achieve a unit radiation dose of 1-35 or 1-36 J/cm$^2$ per exposure or per day; and c) repeating steps a) and b) until a cumulative radiation dose of 150 to 560 J/cm$^2$, or 150-600 J/cm$^2$ during a total treatment period is achieved. In some embodiments, a subject is exposed to radiation no more than once per day.

The invention provides a method of improving the therapeutic efficacy of curcuminoids in the treatment of or a method of treating a disease or disorder having an etiology associated with excessive cell proliferation. The method comprises: a) systemically administering to a subject, having an affected area with a disease or disorder having an etiology associated with excessive cell proliferation, an effective amount 25 to 2500 mg of curcuminoid per day; b) exposing 0.2 m² or greater or 40 cm² or greater of skin of the subject to device-generated visible light radiation having an irradiance (intensity) of 2 mW/cm² or higher for a period of 5-100 min at an irradiation distance of 2-20 inches or 5-50 cm to achieve a radiation unit dose of 1-36 J/cm², the exposing being performed one to four times or two to three times per week; and c) repeating steps a) and b) according to a dosing regimen until a cumulative radiation dose of 150 to 560 J/cm², or 150-600 J/cm² during a total treatment period is achieved.

The invention also provides a method of treating a disease or disorder having an etiology associated with excessive cell proliferation, the method comprising: a) systemically administering to a subject, having an affected area with a disease or disorder having an etiology associated with excessive cell proliferation, an effective amount of curcuminoid per day; b) exposing 0.2 m² or greater or 40 cm² or greater of skin of the subject to device-generated visible light radiation having an irradiance of 2 mW/cm² or higher and a maximum wavelength in the range of 400 to 550 nm and/or of device-generated ultraviolet light having an irradiance of 2 mW/cm² or higher and a maximum wavelength in the range of 315 to 400 nm for a period of 5 min or higher at a irradiation distance of 2-20 inches, 2-10 inches, 10-20 inches or 20 inches to achieve a radiation unit dose of 1 to 18 J/cm², the exposing being performed on a 2 to 4 times or 2 to 3 times per week basis; and c) repeating steps a) and b) according to a dosing regimen until a cumulative radiation dose of 150-200 J/cm² is achieved during a total treatment period of two weeks or more.

The invention also provides a method of treating vitiligo in a subject, the method comprising: a) within a total treatment period, systemically administering to a subject, having an affected area with vitiligo, an effective amount of curcuminoid per day; b) within the total treatment period, exposing 0.2 m² or greater or 40 cm² or greater of skin of the subject to device-generated ultraviolet light radiation having an irradiance of 2 to 300 mW/cm² and a maximum wavelength in the range of 315-400 nm for a period of 5 min or higher at a irradiation distance of 2-20 inches to achieve a radiation unit dose of 1 to 8 J/cm², wherein said exposing is performed on a 3 to 4 times or two times per week basis; and c) repeating steps a) and b) according to a dosing regimen until a cumulative radiation dose of 100 to 150 J/cm² or 120 J/cm² is achieved during a total treatment period of two weeks or more, whereby the affected area is tanned and possesses acceptable pigmentation.

Some embodiments of the invention include those wherein: a) the curcuminoid is present in pure form; b) the curcuminoid is present as a *Curcuma longa* extract, e.g. a hydroalcoholic extract having a Curcuminoid concentration of 12% by wt. or an alcoholic extract having a concentration of Curcuminoid of 90% by wt.; c) the systemic administration is oral or parenteral administration; d) the curcuminoid is administered intraperitoneally; e) the curcuminoid is administered systemically and topically; e) the curcuminoid is any curcuminoid described or listed herein; and/or f) the curcuminoid is not administered topically.

The terms curcumin and curcuminoid are used interchangeably herein. In some embodiments, the therapeutic equivalents of Curcumin (curcuminoid) are *Curcuma longa* extracts (hydroalcoholic extracts having a Curcuminoids concentration of 12% or alcoholic extracts having a concentration of Curcuminoids of 90%).

Some embodiments of the invention include those wherein the subject is a mammal, such as a human or non-human.

Some embodiments of the invention include those wherein: a) the disease or disorder is psoriasis, vitiligo, cancer, tumor, lichen or lymphoma; b) the subject has a PASI index of at least 10 or ranging from 10 to 30; c) PASI reduction in the patient is higher than 75% at completion of the treatment period; and/or d) the disease or disorder is moderate psoriasis, moderate to severe psoriasis or severe psoriasis.

Some embodiments of the invention include those wherein: a) the step of exposing comprises exposing 0.2 m² or greater of skin of the subject to device-generated visible light radiation having an irradiance of 2 mW/cm² or higher and device-generated ultraviolet light radiation having an irradiance of 2 mW/cm² or higher for a period of 5 min or higher effective amount of curcuminoid is not escalated during the treatment period; c) the period of exposing (for unit doses) is escalated during the treatment period; d) the amount of radiation administered in a unit dose per day ranges from 2.5 to 16 J/cm²; e) the unit dose of radiation administered is escalated periodically by increments of 1 to 2.5 J/cm² during the treatment period; f) the treatment period ranges from 2 to 12 weeks, 2 to 10 weeks, 3 to 10 weeks or 3 to 8 weeks; g) the cumulative radiation dose ranges from 170-180 J/cm²; h) the unit dose of UV radiation administered is escalated periodically by increments of 1 to 2.5 J/cm² during the treatment period; and/or i) the step of exposing is conducted within 2 hours after administration of a dose of curcuminoid.

Some embodiments of the invention include those wherein: a) the subject does not suffer hyperpigmentation as a result of the treatment; and/or b) the method provides homogeneous pigmentation of the affected area as a result of treatment.

Some embodiments of the invention include those wherein: a) the visible light source has a maximum wavelength in the range from 315-550 nm or from 400-450 nm; b) the visible light source has a maximum wavelength of about 420 nm; c) the ultraviolet light source has a maximum wavelength in the range from 280 to 400 nm, from 280 to 315 nm (UVB) or from 315 to 400 nm (UVA); d) the ultraviolet light source has a maximum wavelength of about 316 nm; e) the irradiance ranges from 2 to 300 mW/cm² or from 2 to 30 mW/cm²; and/or f) the source of device-generated light radiation is spaced away from the affected area an irradiation distance of 2-20 inches.

In a preferred mode, irradiance of between 2-300 mW/cm² and more preferably irradiances of 2-30 mW/cm² can be used to generate a radiation unit dose of 1-36 J/cm² for visible light and/or 1-18 J/cm² for UV light.

Some embodiments of the invention include those wherein: a) the treatment period is at least three weeks, at least one month, at least two months or more; b) the dosing regimen for curcuminoid is daily administration of a total daily amount of 25 to 2500 mg, 25 to 1500 mg, 25 to 1000 mg, 25 to 750 mg, 25 to 500 mg, 25 to 250 mg, 25 to 100 mg, 50 to 100 mg, 70 to 80 mg, 70 to 75 mg, 100 to 1000 mg, 200 to 1000 mg, 300 to 1000 mg, 400 to 1000 mg, 500 to 1000 mg, 600 to 1000 mg, 700 to 1000 mg, 800 to 1000 mg, about 72 mg or about 850 mg, the total amount being divided up into 1 to 5 or 1 to 3 daily doses; c) the dosing regimen for device-generated light is 1 to 7, 2 to 6, 2 to 4 or 2 times weekly administration of 1 to 36 J/cm² or 2 to 18 J/cm² per administration (unit dose of exposure); d) the total (cumulative) amount of curcuminoid administered during the total treatment period ranges from 1400 mg to 140 g; and/or e) the cumulative radiation dose of device-generated light ranges from 150 to 560 J/cm² or 150 to 600 J/cm².

In some embodiments, Curcumin is administered parenterally (intraperitoneally) in combination with device-generated visible light to inhibit tumor growth in a mammal. In some embodiments, Curcumin alone or device-generated light alone did not inhibit tumor growth in the mammal.

The invention provides all combinations of the aspects, objects, embodiments and sub-embodiments of the invention described herein.

DETAILED DESCRIPTION OF THE INVENTION

The present invention seeks to overcome one or more disadvantages of other methods in the prior art. The use of the phototherapy system of the invention together with the systemic administration of Curcumin or its therapeutic equivalents has higher efficacy than the UV-cabins currently used. The oral administration of Curcumin, Curcuminoids, their metabolites or their prodrugs with periodic overlapping administration of unit doses of visible-ultraviolet light radiation avoids the problems commonly associated with photochemotherapy. By the systemic administration of curcumin or its analogs together with irradiation, therapeutic efficacy of curcumin is improved in vivo and efficacies higher than currently available treatments are achieved. Moreover, the dose of Curcuminoids administered can be, but does not have to be, adjusted (escalated), nor is ultraviolet light radiation required when visible light is used, even though ultraviolet light radiation can be added into the instant methods. Unlike other radiation methods, the radiation unit dose can be escalated during the treatment period thereby reducing the number of phototherapy sessions and the time required for bleaching psoriatic lesions. The present inventors have observed that transaminases are normalized as a result of the instant methods.

When device-generated visible light is employed without device-generated ultraviolet light, secondary effects caused by the ultraviolet light are avoided. This means that the administration of corticosteroids and antihistamines for the treatment of secondary effects caused by radiation can be avoided or minimized, even though the invention can include embodiments wherein such other drugs can also be administered as part of the methods herein. The lack of adverse reactions in curcuminoid therapy and visible light phototherapy renders possible practice of the instant patient in pediatric, elderly and at-risk patients. Since the curcuminoids are administered systemically, the patients' clothes are not stained. The successful treatment of the diseases and disorders herein provide patients with improved emotional state and personal relations. Moreover, patients demonstrate improved compliance with the treatment methods herein as compared to methods employing topical administration of curcuminoids. When the combination of device-generated visible light and device-generated ultraviolet light are used in the instant methods, patients are uniformly tanned without hyperpigmentation. The combined use of curcuminoid with device-generated visible light is not hepatotoxic, and after phototherapy, patients need not be protected from sunlight.

The combination of device-generated visible and/or ultraviolet light with Curcuminoids gives a synergetic effect and may be used for the treatment of all pathologies in which Curcumin might have had potential activity. However device-generated visible light is preferred, as the use of systemic Curcuminoids or their equivalents enables administration of the drug with the main meals and not two hours before radiation, meaning that the curcuminoid can be administered at any time throughout the day and the exposure of the subject to radiation during a 24-hour is independent of when curcuminoid has been administered during the same 24-hour period. The curcuminoid can be administered in the morning, afternoon, evening or night, and the radiation can be independently administered in the morning, afternoon, evening or night. The first dose of radiation is generally administered to a subject after the subject has been administered curcuminoid for a minimum of 1 to 4 days.

As used herein, the term "cumulative radiation dose" is the sum total of all radiation unit doses to which a subject (patient) is exposed during a total treatment period. As used herein, the term "total treatment period" is that period of time starting with administration of the first unit dose of curcuminoid and ending with administration of the final unit dose of curcuminoid to a subject. In terms of irradiation of a subject, a total treatment period can also be that period of time starting with administration of the first unit dose of radiation administered to a subject and ending with administration of the final unit dose of radiation administered to a subject.

As used herein, the term "affected area" refers to an area of skin of a subject having a specified disease or disorder. The affected area is comprised within the area of skin being treated by irradiation.

As used herein, the term "device-generated light" or "device-generated light radiation" refers to radiation generated by a source other than the sun or moon or other natural sources of light. Device-generated light is light generated by an electronic and/or optical device. In some embodiments, device-generated light excludes solar radiation.

As used herein, the term "irradiation distance" refers to the distance between the source of device-generated light and the surface being irradiated by the device-generated light. In some embodiments, the irradiation distance ranges from 2 to 20 inches, 2 to 10 inches, 10 to 20 inches or 5 to 10 inches.

As used herein, the term "effective amount" is taken to mean a pharmaceutically effective amount. A pharmaceutically effective amount is the amount or quantity of curcuminoid which is enough for the required or desired therapeutic response, or in other words, the amount, which is sufficient to elicit an appreciable biological response when, administered to a patient. The appreciable biological response may occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors The invention provides a method of treating various different diseases or disorders with curcuminoid. It also provides a method of improving curcuminoid therapy following oral or parenteral administration thereof. The method requires administering effective amounts of curcuminoid to a subject in need thereof and irradiating one or more affected areas of a subject with device-generated visible light having a maximum wavelength in the range from 315-550 nm or from 400-450 nm and having an irradiance ranging from 2 to 300 mW/cm$^2$ or from 2 to 30 mW/cm$^2$. The source of visible light radiation is spaced away from the affected area an irradiation distance of 2 to 20 inches. The daily effective amount of curcuminoid ranges from 25 to 2500 mg. The treatment area (that area exposed to device-generated visible and/or device-generated ultraviolet light radiation) will include the affected area within it and can have a surface area of 0.2 m$^2$ or more. The method can further comprise a step of irradiating one or more affected areas of a subject with device-generated ultraviolet light having a maximum wavelength in the range from 280 to 400 nm, from 280 to 315 nm (UVB) or from 315 to 400 nm (UVA) and having an irradiance ranging from 2 to 30 mW/cm². The irradiation with device-generated visible light and device-generated ultraviolet light can be performed simultaneously, sequentially or in an overlapping manner.

It should be understood that the unit of radiation dose, e.g. J/cm², refers to the amount (Joules) of radiation per cm² of skin exposed to the radiation. The unit of irradiance, e.g. mW/cm², refers to the irradiance (milliWatts) per cm² of skin exposed to the radiation.

In another aspect, the invention provides a phototherapy system and device for the treatment of proliferative diseases, particularly for the treatment of moderate to severe or severe psoriasis. The phototherapy system comprises a phototherapy device that emits device-generated visible light over a surface area greater than 0.2 m² and with irradiance higher than 2 mW/cm². In a preferred mode, the maximum wavelength is 420 nm and the light source is LEDs, and optionally the device may have an ultraviolet light source in order to promote a good pigmentation and a healthy tan.

Curcuminoids, in the form of Curcumin, alcoholic *Curcuma* extracts (90% Curcuminoids) or hydroalcoholic *Curcuma* extracts (12% Curcuminoids), increase their therapeutic efficacy in vivo when they are systemically administered in combination with visible-ultraviolet light radiation (315-550 nm).

The preparation of apolar and polar extracts containing curcumin, in particular extracts obtained by extraction of *Curcuma longa* plant mass, is described in U.S. Pat. No. 6,440,468 to Quintanilla et al., EP1133992 (equivalent to U.S. Pat. No. 6,841,177 and PCT/ES00/00354 and related to U.S. Pat. No. 7,220,438) to Quintanilla et al., and ES2103689, the entire disclosures of which is hereby incorporated by reference.

Exemplary curcuminoids include curcumin (diferuloylmethane), desmethoxycurcumin (hydroxycinnamoyl feruloylmethane), and/or bis-desmethoxycurcumin (dihydroxydicinnamoyl methane) (see Drug Analysis by Chromatography and Microscopy, p. 169, Ann Arbor Science Inc., 1973), which may be purchased from commercial sources or isolated from turmeric. Methods for isolating curcuminoids from turmeric are known, (see Janaki and Bose, An Improved Method for the Isolation of Curcumin From Turmeric, J. Indian Chem. Soc. 44: 985 (1967)). Alternatively, curcuminoids for use in the present invention can be prepared by synthetic methods. Curcumin not only has anti-oxidant properties but also may have anti-inflammatory, anti-tumor and other valuable properties.

Alternatively, other therapeutic equivalents or analogs of Curcuminoids can be used, for example those described by Anand et al (*Biochem Pharmacol.* (2008) Aug. 19. [Epub ahead of print]), *curcuma* rhizomes or Curcumin cyclised by the action of irradiation increase their in vivo efficacy when concomitantly administered with visible-ultraviolet radiation.

The combination treatment of oral administration of Curcuminoids and irradiation with visible light Curcuminoids exhibits the same efficacy in moderate to severe psoriasis as the combination of oral administration of Curcuminoids and irradiation with ultraviolet light.

Example I describes a clinical trial conducted to evaluate the efficacy of the method of the invention in the treatment of moderate to severe psoriasis with device-generated ultraviolet light over a total treatment period of 8 weeks. The initially PASI of subjects, group according to phototype I, II, III or IV, was determined. Subjects were then administered tablets containing 24 mg curcuminoid three times daily (each tablet taken before a main meal) for a total daily dose of 72 mg. Subjects were treated with UV radiation (UVA, 315-400 nm, 365 nm wavelength maximum) twice weekly for a total of 16 radiation treatments. The initial radiation unit dose was initially 2.5 J/cm², which was escalated by 0.5-1 J/cm² and then by 2 J/cm² until reaching a per day unit dose of 16 J/cm², which dose took about 30 min to administer. After each radiation treatment, the PASI of each subject was determined again. The cumulative radiation dose ranged from 170 to 180 J/cm² during the total treatment period of 8 weeks. All patients achieved the target 16 J/cm² dose and hyperpigmentation resulting from radiation was not observed. By the end of 8 weeks, all patients achieved a PASI reduction of at least 80%.

Accordingly, the invention provides a method of treating moderate to severe psoriasis comprising: systemically (orally) administering to a subject, having a PASI ranging from 10-20, a total of 70 to 80 mg of curcuminoid on a per day basis for a total treatment period of 3 to 8 weeks; and exposing at least 0.2 m² of skin (comprising a psoriatic area) of the subject 2.5 to 16 J/cm² unit doses of device-generated ultraviolet light on a twice weekly basis for a total treatment period of 3 to 8 weeks, thereby providing a PASI reduction of at least 80%. In some embodiments, the total daily dose of curcuminoid is divided into 2 or 3 doses. In some embodiments, the unit dose of radiation is escalated from 2.5 to 16 J/cm² during the treatment period in escalation increments of 0.5 to 1 J/cm². In some embodiments, the unit dose of radiation is maintained level after reaching a target maximum, e.g. after reaching 16 to 18 J/cm². In some embodiments, the cumulative radiation dose during the total treatment period ranges from 150 to 250, 150-200 or 170-180 J/cm².

Example II describes a clinical trail conducted to evaluate the efficacy of the method of the invention in the treatment of moderate to severe psoriasis with visible light over a total treatment period of 8 weeks. The initially PASI of subjects, group according to phototype I, II, III or IV, was determined. Subjects were then administered tablets containing 24 mg curcuminoid three times daily (each tablet taken before a main meal) for a total daily dose of 72 mg. The entire bodies (about 2.4 m²) of naked subjects were treated with visible light (400-550 nm, 420 nm wavelength maximum) twice weekly for a total of 16 radiation treatments. The radiation unit dose was maintained at 18 J/cm², which dose took about 1 hour and 40 min to administer. After each radiation treatment, the PASI of each subject was determined again. By the end of 8 weeks, all patients achieved a PASI reduction of at least 80%.

Accordingly, the invention provides a method of treating moderate to severe psoriasis comprising: systemically (orally) administering to a subject, having a PASI ranging from 10-20, a total of 70 to 80 mg of curcuminoid on a per day basis for a total treatment period of 3 to 8 weeks; and exposing the entire naked body of a psoriatic subject to a unit dose of about 18 J/cm² of visible light on a twice weekly basis for a total treatment period of 3 to 8 weeks, whereby a cumulative radiation dose of 280 to 290 J/cm² is administered to each patient. In some embodiments, the total daily dose of curcuminoid is divided into 2 or 3 doses. In some embodiments, the dose of radiation is maintained level at 18 J/cm², thereby providing a PASI reduction of at least 80%. In some embodiments, the cumulative radiation dose administered during the total treatment period ranges from 250-350, 250-300, 275-300 or 280-290 J/cm².

Example III describes a clinical trial somewhat similar to that of Example II, except that only 40 cm² of treatment area (including the 30-35 cm² of affected area of the back or gluteus of a patient) was exposed to device-generated visible light radiation. Moreover, an irradiation distance of 5 cm and an irradiance of 30 mW/cm$^2$ were used. Also, patients were administered one capsule per day containing 280 mg of curcuminoids. The irradiation doses were escalated from 2 J/cm$^2$ to 16 J/cm$^2$, thereby providing a PASI reduction of at least 90% in each patient over a total treatment period of 8 weeks.

Accordingly, the invention provides a method of treating moderate to severe psoriasis comprising: systemically (orally) administering to a subject, having a PASI ranging from 10-20, a total of 280 mg of curcuminoid on a per day basis for a total treatment period of 3 to 8 weeks; and exposing 40 cm$^2$ (or 30-35 cm$^2$) of treatment area of a psoriatic subject to 2 to 16 J/cm$^2$ of device-generated visible light having an irradiance of 30 mW/cm$^2$ and at an irradiation distance of 5 cm on a twice weekly basis for a total treatment period of 3 to 8 weeks, thereby providing a PASI reduction of at least 90%.

Example IV describes a clinical trail conducted to evaluate the efficacy of the method of the invention in the treatment of vitiligo with ultraviolet light over a total treatment period of 8 weeks. Subjects were then administered tablets containing 24 mg curcuminoid three times daily for a total daily dose of 72 mg. The affected areas of subjects were treated with ultraviolet light (315-400 nm, 365 nm wavelength maximum) twice weekly for a total of 16 radiation treatments. The radiation dose was escalated from an initial dose of 1 J/cm$^2$ to a maintenance dose of 8 J/cm$^2$ using dose escalation increments of 2 J/cm$^2$ until reaching a dose of 7 J/cm$^2$ and then using a dose escalation of 1 J/cm$^2$. By the end of 8 weeks, all patients achieved a significant improvement and enjoyed good homogeneous tanning without hyperpigmentation or burning. The combination of Curcuminoids/ultraviolet light produced pigmentation in the patients treated without causing burns. The combination of Curcuminoids/visible light plus ultraviolet light will allow homogenous pigmentation of all patients who are treated with Curcuminoids/visible light.

Accordingly, the invention provides a method of treating vitiligo comprising: systemically (orally) administering to a subject a total of 70-80 mg or about 72 mg of curcuminoid on a per day basis for a total treatment period of 8 weeks; and exposing the vitiligo affected area of a subject to 1 to 8 J/cm$^2$ of ultraviolet light on a twice weekly basis for a total treatment period of 8 weeks, thereby providing homogeneous or good tanning without hyperpigmentation of the affected area. In some embodiments, the dose of radiation is escalated from 1 to 8 J/cm$^2$ during the treatment period in escalation increments of 1 to 2 J/cm$^2$.

Example V describes a mouse model used to evaluate the efficacy of the method of the invention in the treatment of cancer. Visible light was irradiated on mice and combined with intraperitoneal administration of curcumin to produce a 70% inhibition of the proliferation of human epidermal carcinoma cells (A431). In contrast to *J. Am. Acad. Dermatol.* 2008 April; 58(4):625-31, which reported that Curcuminoids administered at doses of 4.5 g/day lacked efficacy in the treatment of psoriasis, the present inventors have discovered that the combination of Curcuminoids with quantifiable device generated light, either ultraviolet or visible, is effective in treating psoriasis. All patients achieved a PASI reduction of 75% or higher, and no patient abandoned the therapy. In the middle of the trial described herein, in week four (after 8 phototherapy sessions), 50% of patients reached a PASI reduction greater than 75% of baseline. In the middle of trial described herein, the efficacy (therapeutic response) was higher than the therapy with Efalizumab after 12 weeks of treatment and was without secondary (adverse) effects.

Accordingly, the invention provides a method of improving curcuminoid therapy by combining systemic administration of a low amount of curcuminoid with a high amount of visible light radiation. That the inventors were able to demonstrate efficacy with reduced systemic doses of curcumoid in the presence of visible or ultraviolet light is especially surprising, since curcumin is degraded in the presence of light in solution and in solid state.

The combination of visible light and systematically administered Curcuminoids is expected to be effective for the treatment of any tumor type, for example, epidermal, esophageal, duodenum, colon, breast, liver, kidney or prostate. In some embodiments, the cancer or tumor is skin cancer.

In the case of using device-generated visible light, any irradiance and any type of light can be used, for example incoherent, polarized, pulsed or laser due to the absence of secondary effects. The light should have an irradiance ranging from 2 mW/cm$^2$ to 300 mW/cm$^2$ or 2 mW/cm$^2$ to 30 mW/cm$^2$ The curcuminoid and device-generated light are administered to a subject in need thereof according to a specified dosing regimen, which may be the same or can change throughout a treatment period. The curcuminoid can be administered according to a dosing regimen that is the same as or different than the dosing regimen for the device-generated light. Each dosing regimen can comprise once, twice, three, four-times or more per day administration. The per day administration can be repeated in a week one to seven times weekly, every day, every other day, two times per week, three times per week, four times per week, five times per week. The number of weeks per month that the per day administration can be administered can be 1 to 5 weeks per month, weekly, or every other week. The number of months per year that the per day administration can be administered can be 1 to 12 months, monthly, bimonthly, quarterly, trimesterly or biannually. Accordingly, the treatment period for the method of the invention can range from 1 week to 1 year, 1 week to 6 months, 1 week to 8 weeks. The treatment period will end when the desired clinical benefit has been achieved in a subject. If the subject is being treated for psoriasis, the treatment period can end at or after the time point when the subject has experienced at least a 75% reduction or at least an 80% reduction in the PASI score. If the subject is being treated for cancer or tumor, the treatment period can end at or after the time point when the subject has experienced a slowing or reversal of progression or a partial or complete remission.

In some embodiments, curcuminoid is administered according to the following dosing regimen: a) 20-2500 mg per day for a treatment period of 1 to 52 weeks; b) 280-600 mg per day for 8 weeks; or c) other dosing regimen, which may be defined by a clinician and the specific needs, diagnosis, or prognosis of a subject being treated.

In some embodiments, the device-generated light is administered according to the following dosing regimen: a) device-generated light having an irradiance of 2-300 mW/cm$^2$ to achieve a radiation unit dose of 1 to 36 J/cm$^2$ or 1 to 18 J/cm$^2$ per 0.2 m$^2$ of affected area (or of skin treated) in a subject, wherein unit doses are administered on a 1 to 4 times per week basis, for a treatment period of 2 to 10 weeks to provide a cumulative radiation dose ranging from 150 to 580 J/cm$^2$ or 150 to 600 J/cm$^2$; b) device-generated visible light having an irradiance of 2-30 mW/cm$^2$ to achieve a radiation unit dose of 1 to 18 J/cm$^2$ per 0.2 m$^2$ of affected area (or of skin treated) in a subject, wherein unit doses are administered on a 2-times per week basis, for a treatment period of 3 to 8 weeks to provide a cumulative radiation dose ranging from 150 to 200 J/cm$^2$; or c) device-generated visible light having an irradiance of 2-30 mW/cm$^2$ to achieve a radiation unit dose of 17-18 J/cm$^2$ per 0.2 m$^2$ of affected area (or of skin treated) in a subject, wherein unit doses are administered on a 2-times per week basis, for a treatment period of 5 to 8 weeks to provide a cumulative radiation dose ranging from 180 to 300 J/cm$^2$. The radiation unit dose can be escalated by increments of 0.1 to 2 J/cm$^2$, 0.5 to 2 J/cm$^2$, 1 to 2 J/cm$^2$, 1.5 to 2 J/cm$^2$ for UV radiation and 2 to 8 J/cm$^2$ or 2 to 16 J/cm$^2$ or 2 to 32 J/cm$^2$ for visible light.

The combination of Curcuminoids/visible-ultraviolet light is effective therapeutically at doses lower than those described in the state of the art, for example 1-10 mg/kg/day in psoriasis by oral administration or 10-50 mg/kg/day in the inhibition of tumors in a mouse model by intraperitoneal administration.

Thus, formulations comprising at least a Curcuminoid or analog together with excipients acceptable for systemic administration, and optionally other active principles, can be developed. The formulation used in the method is adapted for systemic administration of curcuminoid. Exemplary types of formulations include oral, buccal, parenteral, otic, ophthalmic, nasal, inhalable, sublingual, enteral, oral, peroral, and injectable dosage forms. Particular dosage forms include a solid, suspension, gel or liquid dosage forms. Exemplary suitable dosage forms include tablet, capsule, pill, caplet, troche, sache, solution, suspension, dispersion, vial, ampoule, bag, bottle, syringe, injectable liquid, i.v. (intravenous), i.m. (intramuscular) or i.p. (intraperitoneal) administrable liquid and other such dosage forms known to the artisan of ordinary skill in the pharmaceutical sciences. A dosage form can be packaged using conventional packaging equipment and materials. It can be included in a pack, envelope, packet, blister pack, box or other such container.

A dosage form can be made by any conventional means known in the pharmaceutical industry. A liquid dosage form can be prepared by providing at least one liquid carrier and curcuminoid or curcuminoid-containing extract in a container. One or more other excipients can be included in the liquid dosage form. A solid dosage form can be prepared by providing at least one solid carrier and curcuminoid or curcuminoid-containing extract. One or more other excipients can be included in the solid dosage form.

A liquid, suspension or gel formulation can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

Although not necessary, a formulation or kit of the present invention may include a chelating agent, preservative, antioxidant, adsorbents, acidifying agent, alkalizing agent, antifoaming agent, binding, buffering agent, colorant, diluent, electrolyte, filler, preservative, salt, stabilizer, surfactant, tonicity modifier, other pharmaceutical excipient, or a combination thereof A subject treated according to the invention will exhibit a therapeutic response. By "therapeutic response" is meant that a subject suffering from the disease or disorder will enjoy at least one of the following clinical benefits as a result of treatment with systemically administered curcuminoid and phototherapy: amelioration of the disease or disorder, reduction in the occurrence of symptoms associated with the disease or disorder, partial remission of the disease or disorder, full remission of the disease or disorder, or increased time to progression. In other words, the therapeutic response can be a full or partial therapeutic response.

Once a drug has been discovered that is capable of increasing its efficacy when administered concomitantly with visible light, an expert in the field can develop any phototherapy system comprising the means to emit a visible wavelength (400-550 nm) with an irradiance greater than 2 mW/cm$^2$ on a surface greater than 0.20 m$^2$. Light sources that can be used according to the invention include, for example, gas discharge lamps, LEDs, polarized light, a laser beam or filtered solar radiation.

Among gas discharge lamps emitting in the range of 400-550 nm with a maximum at 420 nm are the Phillips TLK 40W/03 and Phillips TLK 140W/03. Their dimensions are 60*4 cm and 140*4 cm respectively. Ten Phillips TLK 40W/03 lamps at a distance of 45 cm emit 5500 lx, that is a irradiance of 2 mW/cm$^2$. Logically, if the distance between the source and the radiation surface is reduced, the irradiance would increase. A source having an irradiance of 2 mW/cm$^2$ emitting for 20 minutes will give a dose of 3*20*60/1000 J/cm$^2$=3.6 J/cm$^2$. Such lamps can be connected without difficulty to the current phototherapy cabins that use ultraviolet light discharge tubes.

The development of LED technology allows obtaining radiations with a greater luminous efficiency and with a very narrow wavelength emission (±5 nm) and can used in phototherapy. *J Invest Dermatol.* 2002 July; 119(1):77-83 discloses LED panels that radiate over a surface of 30 cm$^2$ with an irradiance of 9-11 mW/cm$^2$, but the distance between the source and the psoriatic plaque was not specified. If the distance between the source and surface irradiated is reduced then irradiance will be greater but irradiation surface area will be smaller. Irradiating at a distance of 5 cm, it is possible to achieve irradiances of 30 mW/cm$^2$ with currently commercially available LEDs.

In the same way, increasing the number of panels of LEDs increases the radiated surface. 60 panels of 12*25 cm, similar to those described in *J Invest Dermatol.* 2002 July; 119(1): 77-83, would irradiate over the whole adult body surface with an irradiance of 30 mW/cm$^2$ at a distance of 5 cm in order to treat the moderate to severe psoriasis.

It should be noted that small spectral variations in radiation or incidence angles will modify the radiometric measurements. For example, radiant energy depends on wavelength of the radiation according to E=hv wherein h is Planck's constant and v is frequency of wavelength, but irradiation sources are not monochromatic and radiometric measurements may vary depending frequency distribution in the irradiation sources.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Example I

Effect of an Orally Administered Hydroalcoholic Extract of *Curcuma longa* in Combination with Ultraviolet Light in Moderate to Severe Psoriasis A pilot clinical trial was designed for the treatment of patients diagnosed with chronic psoriasis with moderate to severe plaques in which other treatments such as cyclosporine, psoralenes/UVA or corticoids had previously failed. The study parameters were as follows.

number of patients: 22.

trial duration: 8 weeks/16 ultraviolet radiation sessions, or two UV radiation sessions per week.

Medication: 24 mg of Curcuminoids per tablet, in the form of hydroalcoholic *Curcuma longa* extract having a Curcuminoids concentration of 12%. The excipients used in the formulation were: cellulose, magnesium stearate, corn starch, sodium starch glycolate, potassium hydrogen phosphate and silicon dioxide. The pH of one tablet dispersed in water (5% w/v) was 5.

Administration regime: 3 tablets/day before main meals (72 mg Curcuminoids/day);

Radiation source: PUVA COMBI LIGHT cabin with 32 lamps of Philips UVA 100 W (315-400 nm, maximum 365 nm).

Irradiated surface: all the naked body surface except genitals of the subjects, approximately 2 m².

Irradiation distance: about 45 cm (the radiation cabin was approximately 80×80 cm² and the patient was placed in the middle of the cabin.

Doses: 2 phototherapy sessions per week were administered. The initial dose was 2.5 J/cm². The dose was increased by 0.5-1 J/cm² until reaching a slight erythema and later increased by 2 J/cm² per session until reaching 16 J/cm². The radiation time to reach 16 J/cm² was approximately 30 minutes.

Rescue medication was used as needed:

a topical emollient formulation containing vitamin B3 for the symptomatic relief of cutaneous manifestations;

oral desloratadine (5 mg), if itching occurred.

The *Curcuma* extract was obtained according the following process: extraction of rhizomes of *Curcuma longa* with ethanol, evaporation of the solvent and quantification of the Curcuminoids content expressed as Curcumin; extraction of the rhizomes of the previous phase with water and evaporation of the solvent; the resultant extracts were mixed and an extract was obtained with a Curcuminoids concentration of 10-15%.

The phototypes of the patients were I, II, III, IV. The average weight was 70 kg. The determination of skin phototype was performed according to the Fitzpatrick Classification Scale.

PASI reduction is detailed in following table for the different visits V1-V16 (2 visits per week). The patients who achieved a PASI reduction of more than 90% left the study.

For example, the doses irradiated to patients, 1, 2, 3 and 9 were:

| | Patient | | | |
|---|---|---|---|---|
| | 1 | 2 | 3 | 9 |
| | | Phototype | | |
| | III | II | I | IV |
| VISIT 1 | 2.5 | 2.5 | 2.5 | 2.5 |
| VISIT 2 | 3.5 | 3.5 | 3.5 | 3.5 |
| VISIT 3 | 4.5 | 4.5 | 4.5 | 4 |
| VISIT 4 | 5.5 | 5.5 | 5.5 | 5 |
| VISIT 5 | 5.5 | 7.5 | 6.5 | 6 |
| VISIT 6 | 7.5 | 9.5 | 8.5 | 8 |
| VISIT 7 | 9.5 | 11.5 | 10.5 | 10 |
| VISIT 8 | 11.5 | 13.5 | 12.5 | 12 |
| VISIT 9 | 13.5 | 15.5 | 14.5 | 14 |
| VISIT 10 | 15.5 | 16 | 15.5 | 15 |
| VISIT 11 | 16 | 16 | 16 | 15.5 |
| VISIT 12 | 16 | 16 | 16 | 16 |
| VISIT 13 | 16 | 16 | 16 | 16 |
| VISIT 14 | 16 | 16 | 16 | 16 |
| VISIT 15 | 16 | 16 | 16 | 16 |
| VISIT 16 | 16 | 16 | 16 | 16 |

The 22 patients reached the radiation of 16 J/cm² and the accumulated dose were of the order of 170-180 J/cm².

No patient abandoned the treatment and radiation was well tolerated without severe photo toxicity reactions. Only one patient received a 5 mg desloratadine tablet.

After the 7th phototherapy session, the patients showed a healthy tan without stains or hyperpigmentations. Hyperpigmentations did not appear in any patient.

Hepatic parameters were within the normal range and hepatotoxicity was not identified. An increase of the red series was observed.

At the end of trial, the patients was pleased with the therapy and the commented that their self-esteem and personal relations had improved.

The results show the potential use of Curcumin, Curcuminoids, metabolites or their prodrugs as sun filters against visible-ultraviolet radiation. That is, hyperpigmentations were not produced in patients with phototypes III and IV and erythema and freckles were avoided in patients with fair skin.

In the middle of the trial, after fourth weeks and only 8 phototherapy sessions, 50% of patients reached PASI reduc-

| PASI Reduction | | | | | | | | | | | | | | | | | | | | | | |
|---|---|---|---|---|---|---|---|---|---|---|---|---|---|---|---|---|---|---|---|---|---|---|
| | Patient | | | | | | | | | | | | | | | | | | | | | | |
| Visit No | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| v1 | 11 | 36 | 42 | 0 | 15 | 24 | 35 | 25 | 0 | 7 | 20 | 13 | 11 | 17 | 32 | 40 | 34 | 48 | 31 | 53 | 49 | 49 |
| V2 | 31 | 51 | 63 | 21 | 43 | 65 | 53 | 35 | 6 | 45 | 17 | 25 | 32 | 21 | 47 | 60 | 61 | 52 | 49 | 54 | 58 | 69 |
| v3 | 25 | 36 | 54 | 35 | 35 | 54 | 55 | 54 | 21 | 39 | 39 | 38 | 44 | 54 | 55 | 78 | 82 | 82 | 61 | 60 | 73 | 65 |
| V4 | 47 | 41 | 63 | 33 | 44 | 69 | 55 | 26 | 30 | 36 | 36 | 47 | 59 | 45 | 40 | 80 | 83 | 84 | 63 | 75 | 79 | 67 |
| V5 | 49 | 50 | 59 | 26 | 47 | 73 | 63 | 42 | 36 | 45 | 51 | 39 | 68 | 66 | 53 | 86 | 85 | 87 | 78 | 75 | 82 | 79 |
| V6 | 26 | 56 | 52 | 40 | 47 | 78 | 70 | 42 | 38 | 37 | 72 | 54 | 73 | 73 | 52 | 82 | 89 | 96 | 80 | 78 | 85 | 85 |
| V7 | 37 | 67 | 47 | 35 | 69 | 78 | 73 | 52 | 40 | 54 | 79 | 63 | 69 | 73 | 62 | 88 | 93 | | 84 | 79 | 87 | 85 |
| V8 | 45 | 67 | 59 | 69 | 69 | 78 | 80 | 67 | 48 | 42 | 77 | 37 | 69 | 77 | 62 | 89 | | | 85 | 85 | 92 | 88 |
| V9 | 57 | 67 | 64 | 67 | 73 | 92 | 80 | 67 | 46 | 50 | 76 | 63 | 69 | 79 | 70 | 89 | | | 91 | 87 | | 93 |
| V10 | 76 | 73 | 71 | 68 | 66 | | 93 | 83 | 44 | 67 | 78 | 67 | 82 | 82 | 70 | 90 | | | 88 | | | |
| V11 | 80 | 77 | 74 | 80 | 69 | | | 81 | 47 | 57 | 86 | 69 | 82 | 85 | 76 | 91 | | | 90 | | | |
| V12 | 79 | 77 | 77 | 74 | 80 | | | 80 | 59 | 69 | 82 | 82 | 89 | 84 | 80 | | | | | | | |
| V13 | 79 | 81 | 84 | 77 | 87 | | | 80 | 70 | 70 | 82 | 86 | 91 | 87 | 80 | | | | | | | |
| V14 | 79 | 87 | 82 | 75 | 89 | | | 83 | 70 | 66 | 89 | 87 | | 86 | 81 | | | | | | | |
| V15 | 81 | 81 | 82 | 77 | 89 | | | 87 | 75 | 78 | 86 | 85 | | 88 | 82 | | | | | | | |
| V16 | 91 | 89 | 87 | 88 | 93 | | | 93 | 76 | 86 | 94 | 87 | | 88 | 82 | | | | | | | | tions higher than 75%. The efficacy in the middle of trial, was similar to that of Efalizumab in 12 weeks and without secondary effects.

All the patients reached a PASI reduction of at least 80%.

Example II

Effect of Orally Administered Hydroalcoholic Extract of *Curcuma longa* in Combination with Visible Light in Moderate to Severe Psoriasis The parameters of this study were as follows.
Number of patients: 10
Duration of trial: 8-weeks/16 phototherapy sessions with visible light.
Medication: 24 mg tablets of Curcuminoids in the form of a hydroalcoholic *Curcuma longa* extract with a Curcuminoids concentration of 12%. The excipients used in the formulation were: cellulose, magnesium stearate, corn starch, sodium starch glycolate, potassium hydrogen phosphate and silicon dioxide. The pH of 1 tablet dispersed in water (5% w/v) was 5. The *Curcuma* extract was obtained as in the above trial.
Administration regime: 3 tablets/day before meals (total of 72 mg Curcuminoids/day)
Radiation source: Phillips TLK 40W/03 lamp giving 5500 lx visible light 100*40 W, 400-550 nm maximum emission 420 nm.
Irradiated surface: 100*60*4 cm=2.4 m$^2$ over the naked body surface.
Irradiation distance: about 45 cm
Irradiation doses: 2 phototherapy sessions per week. The irradiated doses were 18 J/cm$^2$, irradiation time: 1 hour 40 minutes.
Rescue medication was used as needed:
a topical emollient formulation containing vitamin B3 for the symptomatic relief of cutaneous manifestations;
oral desloratadine (5 mg), if itching occurred.
The phototypes of the patients studied were skin types II and III. The average weight was 70 kg.
PASI reduction is detailed in following table for the different visits V1-V16 (2 visits per week). The patients who achieved a PASI reduction higher than 90% left the study.

| | PASI reduction | | | | | | | | | |
|---|---|---|---|---|---|---|---|---|---|---|
| | Patient | | | | | | | | | |
| VISIT | 1 | 2 | 3 | 4 | 5 | 6 | 7 | 8 | 9 | 10 |
| V1 | 23 | 17 | 48 | 30 | 40 | 42 | 37 | 25 | 0 | 30 |
| V2 | 25 | 40 | 54 | 42 | 35 | 50 | 49 | 54 | 12 | 42 |
| V3 | 31 | 38 | 63 | 61 | 44 | 57 | 65 | 46 | 25 | 57 |
| V4 | 39 | 50 | 77 | 62 | 47 | 69 | 69 | 66 | 26 | 66 |
| V5 | 47 | 70 | 80 | 70 | 47 | 75 | 81 | 72 | 39 | 73 |
| V6 | 56 | 78 | 83 | 68 | 69 | 79 | 83 | 72 | 45 | 67 |
| V7 | 45 | 78 | 85 | 69 | 69 | 78 | 86 | 77 | 48 | 67 |
| V8 | 68 | 79 | 89 | 70 | 75 | 88 | 87 | 79 | 59 | 78 |
| V9 | 65 | 86 | 92 | 78 | 79 | 93 | 91 | 83 | 65 | 83 |
| V10 | 70 | 82 | | 80 | 85 | | | 85 | 73 | 85 |
| V11 | 79 | 85 | | 84 | 85 | | | 80 | 76 | 86 |
| V12 | 79 | 84 | | 87 | 91 | | | 84 | 80 | 95 |
| V13 | 79 | 87 | | 85 | | | | 87 | 84 | |
| V14 | 82 | 81 | | 86 | | | | 88 | 84 | |
| V15 | 85 | 89 | | 88 | | | | 88 | 86 | |
| V16 | 85 | 90 | | 89 | | | | 88 | 87 | |

The results obtained show the same efficacy was achieved with visible light as with ultraviolet light (Example I). All the patients exhibited a PASI reduction of more than 80% before 8 weeks of treatment.

The treatment was well tolerated and antihistamines and corticoids were not administered.

Example III

Effect of Orally Administered Alcoholic Extract of *Curcuma longa* in Combination with Visible Light in Moderate to Severe Psoriasis A clinical trial was conducted on 4 patients with average age of 48 years, average weight of 68 kg, diagnosed with moderate to severe psoriasis.

The diagnostic criteria were the PASI on psoriatic plaque on the back or gluteus with a surface area of 30-35 cm$^2$.

The irradiation was carried out with a LED lamp, maximum emission 420 nm (visible light). The irradiation distance was 5 cm with an irradiance of 30 mW/cm$^2$ over a surface of 40 cm$^2$.

After the screening visit to carry out the electrocardiogram and analytical determinations on included patients, the most important plaque with a surface area of between 30-35 cm$^2$ was chosen for each patient.

The patients received one capsule/day containing 280 mg of Curcuminoids, as an alcoholic extract with 90% in Curcuminoids. The selected plaque was irradiated a week after the start of *Curcuma* extract treatment and irradiations continued with two phototherapy sessions per week. The initial radiation dose was 2 J/cm2 and was progressively increased to 16 J/cm$^2$.

The four patients reached a PASI reduction of more than 90% of baseline after 8 weeks on the irradiated plaque.

Example IV

Effect of Orally Administered Hydroalcoholic Extract of *Curcuma longa* in Combination with Ultraviolet Light in Vitiligo Six patients diagnosed with vitiligo were treated with 3 tablets/day of an hydroalcoholic extract of *Curcuma* (72 mg Curcuminoids/day) and irradiation in a UV-cabin (315-400 nm, maximum 365 nm). The initial dose was 1 J/cm$^2$ and was increased (escalated) by 2 J/cm$^2$ up to 7 J/cm$^2$. The last irradiation sessions were at 8 J/cm$^2$. A summary of the patients' initial symptomology, treatment and outcome observed follows.

| Patient | Presenting | Treatment | Outcome |
|---|---|---|---|
| 1 | Generalized vitiligo with a large facial patch. | 8 phototherapy sessions. | A quick tan was achieved without burns or erythema |

-continued

| Patient | Presenting | Treatment | Outcome |
| --- | --- | --- | --- |
| 2 | Vitiligo with patches on hands, chin and legs. | 8 phototherapy sessions of 12 J/cm$^2$ on the hands. | Pigmentation foci appeared on the edges of some vitiligo patches. |
| 3 | Extensive vitiligo associated with fibromyalgia and thyroid disorder | 8 phototherapy sessions. | Good tanning. The re-pigmentation process was observed on the neck. |
| 4 | Extensive vitiligo. Hypothyroidism. | 8 phototherapy sessions. | Rapid increase in tan without burns. Pigmentation appeared on the abdomen. |
| 5 | Extensive vitiligo with large facial patches | 8 phototherapy sessions. | Good tanning without burning. Appearance of pigmentation of face and neck. |
| 6 | Extensive vitiligo with large facial patches. | 8 phototherapy sessions. | Good tanning. Vitiligo on the joints. Presence of pigmentation on the elbows. |

Example V

Effect of Curcumin by Intraperitoneal Administration on Inhibition of Tumor Growth in Mice in Combination with Visible Light $5*10^6$ A431 cells (human epidermal carcinoma) were injected subcutaneously into the left and right flanks of athymic nude mice (NMRI) (5-6 weeks old, 20-24 g). The mice were fed in pathogen-free conditions. The animals were fed ad libitum with sterilized food. The animals were sterilized with ketamine/xylazine. For the treatment, 5 mg Curcumin were dissolved first in 50 µl of ethanol and further diluted in 2 ml of 1% methylcellulose and sterilised. The mice were fed intraperitoneally twice a day with 200 µl of the solution or methylcellulose solution alone at a dose of 50 mg Curcuminoids/kg per day.

After intraperitoneal injection, one group of mice (Curcumin and methylcellulose) was irradiated for 20 minutes with 5500 lx. The irradiation device was 10 Phillips TLK 40W/03 lamps (60 cm length*4 cm diameter), at a distance of 45 cm. The emission range of the lamps was between 400-550 nm with a maximum at 420 nm.

Three groups (the control group, methylcellulose group and Curcumin without irradiation group) were protected from light for 1 hour after infection. Tumor size was measured initially and after 10-12 days; afterwards tumor volumes and weights were determined twice a week. At the end of the experiment (29 days), the animals were anesthetized and sacrificed.

The results demonstrate that only the group treated with Curcumin and visible light showed a significant difference in inhibition of tumor growth compared with the control group. The average tumor volume at day 12 in Curcumin/light treated mice was reduced by 70% in comparison to control mice. The tumor volume of the Curcumin-treated but not irradiated group was not significantly reduced (p=0.16), that is visible light improved the efficacy of Curcuminoids in vivo.

As used herein, the term "about" or "approximately" is taken to mean ±10%, ±5%, ±2.5% or ±1% of a specified value.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of treating cancer or tumor, the method comprising:
   a) systemically administering to a subject, having cancer or tumor, an effective amount of curcuminoid, wherein the cancer or tumor is of the skin, esophagus, duodenum, colon, breast, liver, kidney or prostate or is lymphoma;
   b) exposing 0.2 m$^2$ or greater or 40 cm$^2$ or greater of skin of the subject to device-generated radiation having an irradiance of 2 mW/cm$^2$ or higher to achieve a unit radiation dose of 1-36 J/cm$^2$, wherein the radiation comprises visible light radiation and optionally further comprises ultraviolet light radiation; and
   c) repeating steps a) and b) until a cumulative radiation dose of 150 to 600 J/cm$^2$ during a period is achieved.

2. A method of claim 1 comprising:
   a) systemically administering to a subject, having cancer or tumor, an effective amount of curcuminoid per day, wherein the cancer or tumor is of the skin, esophagus, duodenum, colon, breast, liver, kidney or prostate or is lymphoma;
   b) exposing 0.2 m$^2$ or greater of skin of the subject to device-generated visible light radiation having an irradiance of 2 mW/cm$^2$ or higher and an emission maximum wavelength in the range of 400 to 550 nm and, optionally to device-generated ultraviolet light having an irradiance of 2 mW/cm$^2$ or higher and an emission maximum wavelength in the range of 315 to 400 nm for a period of 5 min or higher at an irradiation distance of 2-20 inches to achieve a radiation unit dose of 1-36 J/cm$^2$, the exposing being performed on a 2 to 4 times per week basis; and
   c) repeating steps a) and b) according to a dosing regimen until a cumulative radiation dose of 150-600 J/cm$^2$ is achieved during a period of two weeks or more.

3. The method of claim 2, wherein the device-generate radiation comprises visible light radiation and ultraviolet light radiation.

4. The method of claim 3, wherein the device-generated visible light radiation has an irradiance of 2 mW/cm$^2$ or higher and the device-generated ultraviolet light radiation has an irradiance of 2 mW/cm$^2$ or higher for a period of 5 min or higher.

5. The method according to claim 2 comprising exposing greater than 10% of the body surface area of the skin of the subject.

6. The method of claim 2, wherein the dose of curcuminoid administered is 1-50 mg/kg/day, 25 to 2500 mg per day, or wherein the cumulative dose of curcuminoid administered ranges from 1400 mg to 140 g.

7. The method of claim 2, wherein the curcuminoid is administered at a dose of 1-40 mg/kg/day or 10-50 mg/kg/day.

8. The method according to claim 2, wherein the curcuminoid is present in pure form or in the form of *Curcuma longa* extract.

9. The method of claim 8, wherein the extract is hydroalcoholic or alcoholic extract.

10. The method of claim 9, wherein the extract is a hydroalcoholic extract having a Curcuminoid concentration of 12% by wt. or an alcoholic extract having a concentration of Curcuminoid of 90% by wt.

11. The method of claim 1, wherein the device-generated light is generated by a light source comprising LEDs.

12. The method of claim 1 comprising exposing 1.0 to 2.0 $m^2$ of skin of the subject.

13. The method of claim 1, wherein the irradiance is less than 300 $mW/cm^2$.

14. The method of claim 1, wherein the dose of curcuminoid administered is 1-50 mg/kg/day, 25 to 2500 mg per day, or wherein the cumulative dose of curcuminoid administered ranges from 1400 mg to 140 g.

15. The method of claim 1, wherein the curcuminoid is administered at a dose of 1-40 mg/kg/day or 10-50 mg/kg/day.

16. The method according to claim 1, wherein the curcuminoid is present in pure form or in the form of *Curcuma longa* extract.

17. The method of claim 16, wherein the extract is hydroalcoholic or alcoholic extract.

18. The method of claim 17, wherein the extract is a hydroalcoholic extract having a Curcuminoid concentration of 12% by wt. or an alcoholic extract having a concentration of Curcuminoid of 90% by wt.

19. The method according to 1, wherein:
   a) the visible light radiation has an emission maximum wavelength in the range from 315-550 nm or from 400-450 nm;
   b) the visible light radiation has an emission maximum wavelength of about 420 nm;
   c) the ultraviolet light radiation has an emission maximum wavelength in the range from 280 to 400 nm, from 280 to 315 nm (UVB) or from 315 to 400 nm (UVA);
   d) the ultraviolet light radiation has an emission maximum wavelength of about 316 nm; and/or
   e) the irradiance ranges from 2 to 300 $mW/cm^2$ or from 2 to 30 $mW/cm^2$.

20. The method according to claim 1, wherein the source of device-generated light radiation is spaced away from the affected area an irradiation distance of 2 to 20 inches.

21. The method according to claim 1, wherein the Curcuminoid is administered systemically and topically or administered orally and topically.

22. The method of claim 1, wherein the cancer or tumor is of the skin.

23. A method of treating cancer or tumor, the method comprising:
   a) systemically administering to a subject, having an affected area with cancer or tumor, an effective amount of curcuminoid, wherein the curcuminoid is curcumin, wherein the cancer or tumor is of the skin, esophagus, duodenum, colon, breast, liver, kidney or prostate or is lymphoma;
   b) exposing at least the affected area to device-generated radiation comprising visible light radiation, and optionally further comprising ultraviolet light radition, having an irradiance of 2 $mW/cm^2$ or higher to achieve a unit radiation dose of 1-36 $J/cm^2$; and
   c) repeating steps a) and b) during until a cumulative radiation dose sufficient to ameliorate the cancer or tumor is achieved.

24. The method of claim 23, wherein the cumulative radiation dose is sufficient to provide a partial or full remission of the cancer or tumor.

25. The method of claim 23, wherein the curcuminoid is present in pure form or in the form of a *Curcuma longa* extract.

26. The method of claim 25, wherein the extract is hydroalcoholic or alcoholic extract.

27. The method of claim 26, wherein the extract is a hydroalcoholic extract having a Curcuminoid concentration of 12% by wt. or an alcoholic extract having a concentration of Curcuminoid of 90% by wt.

28. The method of claim 23, wherein the dose of curcuminoid administered is 1-50 mg/kg/day, 25 to 2500 mg per day, or wherein the cumulative dose of curcuminoid administered ranges from 1400 mg to 140 g.

29. The method of claim 23, wherein the curcuminoid is administered at a dose of 1-40 mg/kg/day or 10-50 mg/kg/day.

30. The method of claim 23, wherein the device-generate radiation comprises visible light radiation and ultraviolet light radiation.

31. The method of claim 23, wherein the exposing is conducted 1-4 times per week for a period of 2 to 10 weeks.

32. The method of claim 23, wherein the curcuminoid is present in an oral, parenteral, intraperitoneal, enteral, peroral, or injectable dosage form.

33. The method according to 23, wherein:
   a) the visible light radiation has an emission maximum wavelength in the range from 315-550 nm or from 400-450 nm;
   b) the visible light radiation has an emission maximum wavelength of about 420 nm;
   c) the ultraviolet light radiation has an emission maximum wavelength in the range from 280 to 400 nm, from 280 to 315 nm (UVB) or from 315 to 400 nm (UVA);
   d) the ultraviolet light radiation has an emission maximum wavelength of about 316 nm; and/or
   e) the irradiance ranges from 2 to 300 $mW/cm^2$ or from 2 to 30 $mW/cm^2$.

34. The method according to claim 23, wherein the source of device-generated light radiation is spaced away from the affected area an irradiation distance of 2 to 20 inches.

35. The method of claim 23, wherein the Curcuminoid is administered systemically and topically or administered orally and topically.

36. The method of claim 23, wherein the cancer or tumor is of the skin.

* * * * *